United States Patent [19]

Kiovsky et al.

[11] 4,045,461

[45] Aug. 30, 1977

[54] HIGH TEMPERATURE METHANATION WITH MOLTEN SALT-BASED CATALYST SYSTEMS

[75] Inventors: Thomas E. Kiovsky; Milton M. Wald, both of Houston, Tex.

[73] Assignee: Shell Oil Company, Houston, Tex.

[21] Appl. No.: 666,828

[22] Filed: Mar. 15, 1976

Related U.S. Application Data

[62] Division of Ser. No. 546,371, Feb. 3, 1975, Pat. No. 3,979,332.

[51] Int. Cl.$^2$ .......................... C07C 1/02; C07C 1/04
[52] U.S. Cl. .............................................. 260/449 M
[58] Field of Search ................... 260/449 M, 449.6 M

[56] References Cited

U.S. PATENT DOCUMENTS

| | | | |
|---|---|---|---|
| 3,355,376 | 11/1967 | Gorin et al. | 252/441 |
| 3,453,146 | 7/1969 | Bawa et al. | 252/373 |
| 3,488,226 | 1/1970 | Baker et al. | 252/466 J |
| 3,619,144 | 11/1971 | Bawa et al. | 252/373 |
| 3,625,665 | 12/1971 | Thompson | 260/449 M |
| 3,677,932 | 7/1972 | Hardesty et al. | 252/441 |
| 3,679,577 | 7/1972 | Wantland et al. | 252/441 |
| 3,689,240 | 9/1972 | Aldridge et al. | 48/202 |
| 3,730,694 | 5/1973 | Wunderlich | 260/449 M |
| 3,901,667 | 8/1975 | Hermann | 260/449 M |
| 3,912,775 | 10/1975 | Broecker et al. | 260/449.6 A |
| 3,954,424 | 5/1976 | Goeke et al. | 260/449 M |

OTHER PUBLICATIONS

Breck et al., Alien Property Custodian No. 292742, July 1943.

Breck et al., Alien Property Custodian No. 393258, July 1943.

*Primary Examiner*—Howard T. Mars
*Attorney, Agent, or Firm*—Dean F. Vance

[57] ABSTRACT

The reaction of hydrogen and carbon oxides (carbon monoxide and carbon dioxide) to form methane at temperatures above 500° C is promoted by carrying out the reaction in the presence of a molten metal salt-based catalyst system comprising a molten metal salt carrier selected from the class consisting of the halides and carbonates of alkali metals and alkaline earth metals and the halides of zinc, copper, manganese, cadmium, tin and iron, and mixtures thereof, melting below 1000° C; said molten salt having dispersed therein one or more catalytically active metals selected from the class consisting of iron, molybdenum, manganese, nickel, cobalt, zinc, titanium, silver, copper and thorium in the form of finely divided elemental metals, metal oxides and/or metal carbides.

11 Claims, No Drawings

HIGH TEMPERATURE METHANATION WITH MOLTEN SALT-BASED CATALYST SYSTEMS

This is a division of application Ser. No. 546,371, filed Feb. 3, 1975 now U.S. Pat. No. 3,979,332.

BACKGROUND OF THE INVENTION

This invention relates to catalytic methanation or hydrogenation of carbon oxides to methane and to a catalyst system for effecting same. More particularly, this invention is directed to a methanation process carried out at high temperatures and a molten metal salt-based heterogeneous catalyst system which is uniquely suited for such high temperature methanation.

Catalytic methanation is a well-known reaction which is widely employed in the chemical and energy providing industries. Probably its most widespread current and potential application is in the treatment of the gaseous effluent from the gasification or partial oxidation of carbonaceous fuels with oxygen and/or water, e.g., steam-hydrocarbon reforming and partial combustion of liquid and solid carbonaceous fuels, to produce a hydrogen-rich gas for chemical synthesis, e.g., ammonia manufacture, or petroleum refining, e.g., catalytic hydrocracking and hydrogenation, or to form a methane-rich gas having high BTU value and low CO content for use in residential and industrial heating or power generation. In the former case, the gasification or partial oxidation effluent, which typically contains substantial quantities of $H_2$, $CO$, $CO_2$ and $H_2O$ as well as $N_2$ in cases where air is used as the oxidant source, is generally subject to a process known as the carbon-monoxide shift-conversion reaction prior to catalytic methanation. In this case the CO-shift reaction converts a substantial quantity of the CO present to $H_2$ and $CO_2$ by reaction with $H_2O$ in the presence of a catalyst and the primary purpose of the catalytic methanation is to remove small quantities of CO which remain in the hydrogen-rich product gas by conversion to methane in order to avoid poisoning of downstream processing catalysts. In the latter case, i.e., conversion of partial oxidation effluent gas to methane-rich gas, the gasification or partial oxidation effluent gas is subject to CO-shift to obtain the appropriate ratio of $H_2$ to $CO$ (usually 3 to 1) and the CO shift product gas is then subject to catalytic methanation for conversion of carbon oxides and hydrogen contained therein to methane. In either case, the CO-shift effluent gas is subject to an intermediate processing step to remove sulfurous materials in cases where a sulfur-containing carbonaceous fuel feedstock is employed since all commercially used methanation catalysts are highly sensitive to poisoning by sulfur compounds.

Because of the increasing demand for a high BTU, clean gas as an energy source in the United States and the acknowledged decreasing and finite nature of natural gas reserves in the United States as well as happenings on the world scene which make energy self-sufficiency desirable or even essential, there has been a dramatic increase in interest in the manufacture of a clean, high BTU gas energy which will meet pipeline standards by synthetic means from alternative carbonaceous resources such as coal or heavy hydrocarbons. Many of the more attractive synthetic approaches which have been proposed are based on gasification or partial combustion of the carbonaceous material, and, as indicated above, include catalytic methanation as part of the integrated process scheme to upgrade the BTU value of the product gas to a level acceptable for pipeline gas applications. CO and $H_2$ have heating values of about 300 BTU/ft³ whereas pipeline natural gas has a value above 1000 BTU/ft³. While a number of metallic species are known to be active and selective methanation catalysts including, inter alia, nickel, ruthenium, cobalt, iron and molybdenum, their application to the manufacture of high BTU or pipeline gas has been less than satisfactory for several reasons which relate to the physical form of the catalyst employed and/or the nature of the methanation reaction, itself.

In the first place, the primary thrust of previous efforts to effect catalytic methanation has been to utilize the active catalyst in solid form as a finely divided particulate on a refractory support, i.e., nickel on alumina or kieselguhr being pre-eminent, or as an alloy in a fixed or fluidized bed. These catalyst types are highly susceptible to inactivation via carbon deposition which can only be partially remedied by operation at undesirably high $H_2/CO$ mole ratios in the feed gas. Furthermore, methanation reactions with these catalyst systems generally must be limited to temperatures below 400° C to avoid sintering and deactivation of the catalyst and the highly exothermic nature of the methanation reaction itself provides severe operational difficulties in controlling catalyst temperature in a fixed or fluidized bed at these levels when the CO concentration of the feed gas is in the range required for methane-rich gas manufacture. As an aside the use of the fixed or fluidized bed catalyst processing techniques also make it extremely difficult to recover any substantial quantity of the heat generated in the methanation for use in other phases of the process, e.g., the endothermic gasification in steam gasification of coal. Finally, the methanation reaction itself, is considered to be a combination of several reactions including the primary reaction (1)

$$3 H_2 + CO \rightarrow CH_4 + H_2O \quad (1)$$

and secondary reactions (2) and (3)

$$2 H_2 + 2CO \rightarrow CH_4 + CO_2 \quad (2)$$

$$4 H_2 + CO_2 \rightarrow CH_4 + 2H_2O \quad (3)$$

whose thermodynamic equilibria are such that the equlibriun yield of methane is adversely effected at high temperatures, i.e., above 500° C; reaction (2) being a combination of reaction (1) and the water gas shift reaction (4)

$$CO + H_2O \rightarrow CO_2 + H_2 \quad (4)$$

Thus with conventional catalyst systems, methanations have been limited to the lowest temperatures consistent with acceptable catalyst activity in part, because of catalyst instability at high temperatures, the highly exothermic nature of the methanation reaction and the inability to effect an equilibrium shift towards methane, e.g., by absorption of one of the reaction products, at high temperatures under practical circumstances. A good review of previous efforts in catalytic methanation and the problems associated therewith can be found in G. A. Mill et al., "Catalytic Methanation", *Catalysis Reviews*, 8 (2), 159–210 (1973).

Accordingly, it would be desirable if an active catalyst system for methanation at temperatures above 500° C could be developed which would minimize operational problems associated with high temperature operation of the solid, particulate catalysts of the prior art, e.g., carbon deposition, instability and heat removal, while at the same time somehow shifting the methanation equilibrium towards methane formation, e.g., by $H_2O$ absorption from the reaction mass, at these high temperatures. This would be espcially advantageous when catalytic methanation is utilized in conjunction with, for example, steam gasification of coal for the production of methane-rich gas. This is because the coal gasification reaction is high temperature but endothermic, thus requiring substantial input of high temperature heat such as that which could be recovered from an exothermic methanation reaction carried out at high temperatures. Furthermore, the reaction effluent from such coal gasification is many times already at or close to the thermodynamic equilibrium concentration of methanation reactants in a high temperature methanation reaction scheme, due to the high steam concentration of the gaseous effluent, and as such cannot be catalytically promoted towards methane formation unless one of the reaction products, particularly $H_2O$, is absorbed out of the reaction mass during or prior to methanation.

SUMMARY OF THE INVENTION

It has now been found that certain molten salt-based heterogeneous catalyst systems are active in promoting the methanation of carbon oxides at temperatures above 500° C. These catalyst systems, which comprise molten metal salts or salt mixtures that melt below 1000° C but are stable under methanation conditions at temperatures above 500° C and contain certain active metallic species for catalytic methanation in finely divided form, are less susceptible to carbon deposition than previous catalyst systems, exhibit little, if any, catalyst sintering and inactivation at high temperatures and provide a superior means for reducing the problems associated with heat transfer from the exothermic methanation reaction since the molten salt carrier functions as both a heat sink and a heat exchange medium for the reaction. Furthermore, the molten salt carriers of the invention are effective in absorbing water from the methanation reaction mass at high temperatures, and, as such, function to shift the reaction equilibrium towards methane which is especially critical in cases such as steam gasification of coal where the reactant mass approaches equilibrium concentration of reactants and reaction products at the high temperature methanation conditions, without an intermediate $H_2O$ removal step.

Accordingly, in its broadest aspects the instant invention provides a process for the preparation of methane from a gaseous reactant mixture containing hydrogen, carbon monoxide and/or carbon dioxide which comprises contacting said gas mixture in a reaction zone maintained at temperatures above about 500° C with a molten metal salt-based catalyst system comprising a molten metal salt carrier selected from the class consisting of the halides and carbonates of alkali metals and alkaline earth metals and the halides of zinc, copper, manganese, cadmium, tin and iron, and mixtures thereof, melting below 1000° C; said molten salt having dispersed therein one or more catalytically active metals selected from the class consisting of iron, molybdenum, manganese, nickel, cobalt, zinc, titanium, silver, copper and thorium in the form of finely divided elemental metals, metal oxides and/or metal carbides. Preferably, the gaseous reactant mixture is derived from the partial oxidation or gasification of a carbonaceous fuel and as such also contains a significant amount of water in the form of steam. Also within the scope of the instant invention are the novel molten salt-based catalyst systems, as hereinbefore described, which are active in the high temperature methanation reaction.

DESCRIPTION OF THE PREFERRED EMBODIMENTS

The Catalyst

The high temperture methanation catalysts according to the invention are heterogeneous catalyst systems comprising a molten metal salt carrier which melts below 1000° C, but is stable under methanation reaction conditions at temperatures above 500° C, preferably about 500° to about 800° C, and which contains a uniform dispersion of a finely divided metal, metal oxide and/or metal carbide of certain metallic species which exhibit catalytic activity for hydrogenation of carbon oxides or methanation. To function as an effective carrier in the heterogeneous catalyst system it is essential that the molten metal salt melt be thermally and chemically stable under methanation reaction zone conditions. That is, the molten salt or salt mixture must not be hydrolyzed significantly with steam at temperatures above 500° C nor be reduced by the methanation reactant feed mixture under the conditions prevailing in the reaction zone. Preferably, the metal salt or salt mixture melts below about 700° C and most preferably between about 100° and 600° C. Suitable metal salts or salt mixtures include the halides and carbonates of alkali metals and alkaline earth metals and the halides of zinc, copper, manganese, cadmium, tin and iron or mixtures thereof. Preferred metal salts or salt mixtures are mixtures of alkali metal halides, mixtures of alkali metal carbonates, for example the ternary eutectic of lithium, sodium and potassium carbonate; and the halides of zinc, tin and iron, the latter metal halide hving a minor amount of alkali metal halide added thereto as a melting point depressant. Most preferred because of their availability and/or favorable effect on the activity of the active metallic species in the catalyst system are the zinc halides, e.g., zinc chloride, zinc bromide and zinc iodide; mixtures of an iron halide with a sodium and/or potassium halide, e.g., iron chloride-sodium chloride mix; and the ternary eutectic of lithium, sodium and potassium carbonate. The zinc halides are emminently suitable as molten catalyst carriers in the methanation of gaseous reactant mixtures containing substantial quantities of water such as that derived from the steam gasification of coal since they absorb up to 90% or more of the water present in a typical gasification effluent at methanation temperatures above 500° C and thereby shift the methanation equilibrium towards methane formation.

The active catalytic species in the molten salt-based methanation catalysts according to the invention are finely divided metals, metal oxides and/or metal carbides of certain transition and actinide elements and zinc which are uniformly dispersed in the molten carrier. While this group of catalytically active metals does include certain metallic species which have heretofore been described as having catalytic activity in methanation reactions, e.g., nickel and iron, it is not completely apparent that the instant dispersed solid catalysts function in a manner equivalent to the prior art supported catalysts. This is because only certain of the known methanation catalysts are active in the molten salt-based catalysts of the invention and a metal, zinc, not previously considered to have catalytic methanation activity is, in fact, quite active as a methanation catalyst in the molten-salt based systems of the instant invention. The metals which show catalytic methanation activity when dispersed as finely divided elemental metals, metal oxides and/or metal carbides in the molten salt-based catalysts of the invention include iron, molybdenum, manganese, nickel, cobalt, zinc, titanium, silver, copper and thorium. Of these catalytically active metals, iron, zinc, manganese and molybdenum seem to provide the highest activity and are preferred for that reason. Most preferred for reasons of availability and activity are zinc and iron. As indicated above, the solid metallic catalyst is present in the molten salt carrier as the elemental metal, metal oxide and/or metal carbide. Usually it is present as a mixture of all three chemical forms with the elemental metal and metal oxide being predominant. While the exact particle size of the finely divided metal catalyst in the molten salt carrier is not considered critical to the operability of the invention, it appears that this average particle size diameter should not exceed about 0.5 mm, if optimum results are to be obtained.

The concentration of active metal catalyst dispersed in the molten salt-based catalyst systems of the invention is not critical and will depend, in part, on the concentration of carbon oxides and hydrogen in the reactant gas; the purpose and extent of methanation desired, i.e., production of methane-rich, high BTU gas or conversion of CO to methane in the production of a hydrogen-rich synthesis gas; and process conditions such as reactant feed rates, temperatures, pressures, etc. For most applications, the concentration of active metal catalyst dispersed in the molten salt carrier will range from about 0.1 to about 20% by weight of the total (catalyst + carrier) catalyst composition. Preferably, in cases where the catalyst is employed to upgrade partial oxidation or gasification effluent gas to methane-rich, high BTU gas, the catalyst concentration will range from about 5% to about 15% by weight of the total catalyst composition. As indicated previously this catalyst concentration may be composed of a single catalytically active metal or a mixture of one or more of such metals. Preferred metal mixtures include zinc-iron, iron-manganese and zinc-manganese.

The active catalysts according to the invention may be prepared by simple physical comminution of the metal catalysts, in the form of relatively pure elemental metals or metal oxides, to the desired paticle size, e.g., hammer mill grinding, and subsequent addition of the ground metal or metal oxide powder to the metal salt carrier before or after heating to, or above, its melting point. Alternatively, the active metal catalysts may be prepared by adding the catalytically active metal to the metal salt before or after heating in the form of a compound or complex which will thermally and/or chemically decompose at methanation temperatures into the desired metal and/or metal oxide. Examples of suitable metal compounds or complexes which will decompose to yield the desired metal or metal oxide at methanation temperatures e.g., 500° C or above, include inorganic metal hydroxides and salts such as nitrates and carbonates; organic salts or carboxylic acids such as formate, trifluoroacetate, butrate, 2-ethylhexanoate, lactate and citrate; organo metal compounds and complexes as metalocenes, e.g., ferrocene, metal carbonyls, e.g., iron pentacarbonyl, molybdenum hexacarbonyl, etc., and metal complexes such as those derived from pyridine and the metal acetate or 1-5-cycloactadiene and the metal nitrate. It is also possible to prepare the dispersed metal or metal oxide in situ in the molten salt medium by adding two chemical compounds which will react, e.g., zinc bromide and sodium carbonate, in the molten medium to yield the desired active catalyst, e.g., zinc oxide. In this alternative method of preparing the active catalyst, the thermally and/or chemically decomposable metal compound or complex is preferably added to the metal salt carrier after the carrier has been heated to or above its melting point (usually about 400° C or above) and the molten salt or salt mixture is agitated for a time period ranging from 10 to 120 minutes to allow the metal compound or complex time to decompose and disperse in the molten medium. Preferred metal compounds or complexes for use in this procedure include the metal carbonyls and metalocenes. In this case the gaseous reactants can be contacted by the molten catalyst system prior to decomposition of all of the metal catalyst compound or complex precursor, since the precursor will continuously decompose and release active catalyst during the course of the methanation reaction.

The Process

As indicated above, the molten salt-based catalyst systems of the invention have been found to be active in promoting methanation reactions at high temperatures, e.g., 500° C and above, heretofore considered to be prohibitive due to catalyst deactivation and instability, physical limitations on heat removal and methanation reaction equilibrium. Thus, in one aspect the instant invention contemplates a process for the preparation of methane from a gaseous reactant mixture containing hydrogen, carbon monoxide and/or carbon dioxide which comprises contacting said gas mixture in a reaction zone maintained at temperture above about 500° C with a molten metal salt-based catalyst system comprising a molten metal salt carrier selected from the class consisting of the halides and carbonates of alkali metals and alkaline earth metals and the halides of zinc, copper, manganese, cadmium, tin and iron, and mixtures thereof, melting below 1000° C; said molten salt having dispersed therein one or more catalytically active metals selected from the class consisting of iron, molybdenum, manganese, nickel, cobalt, zinc, titanium, silver, copper and thorium in the form of finely divided elemental metals, metal oxides and/or metal carbides.

The gaseous reactant feed to the catalytic methanation process of the invention must contain at least some measurable amount of hydrogen and carbon oxides (carbon dioxide and/or carbon monoxide). Preferably, the reactant feed mixture to methanation contains both hydrogen and carbon monoxide at an $H_2$:CO mole ratio of 2:1 with $H_2$:CO reactant mole ratios of 3:1 or more being most preferred. Gaseous reactant feed mixtures which can be suitably methanated with catalyst compositions of the instant invention typically contain 10 to 99.9% $H_2$, 0.1 to 501% CO, 0 to 20% $CO_2$, 0 to 70% $H_2O$, 0 to 25% $CH_4$ and 0 to 70% $N_2$. Such gaseous reactant feed mixtures are quite suitably obtained from conventional partial oxidation or gasification of carbonaceous fuels such as, inter alia, natural gas or normally gaseous hydrocarbons, e.g., $C_{2-4}$ saturated and olefinic hydrocarbons; heavier hydrocarbon fractions including gasoline, kerosene, naphtha, distillates, gas oils and residual oils; solid or semi-solid fuels including coal, oil shale, partial combustion soot and bituminous residues from petroleum refining. Typically, the partial oxidation or gasification effluent gas will be subject to a conventional CO-shift reaction to adjust the hydrogen to carbon monoxide mole ratio and an optional particulate removal step, e.g., one or more cyclone separators, prior to methanation according to the invention. However, at least the intermediate CO-shift step is not essential to the preparation of a suitable gaseous feedstock for use in the invention since conversion of reactants to methane will still be effected to the extent that the stoichiometry of the reaction can be satisfied. Since all of the catalyst compositions according to the invention exhibit at least some sensitivity to sulfur poisoning, it is essential that either a desulfurized carbonaceous fuel be employed in the reactant gas generating process or that the reactant gas be subject to a conventional desulfurization procedure i.e., scrubbing with liquid or solid absorbents for sulfur compounds (mainly $H_2S$) prior to contact with the molten methanation catalysts of the invention.

One of the preferred applications of the catalytic methanation process of the instant invention is in the upgrading of methane-rich gas derived from the partial oxidation or gasification of coal. Several coal gasification processes employing non-catalytic gasifiers in which coal is converted to a crude product gas containing principally $CH_4$, $H_2$, CO, $H_2O$ and $CO_2$ by high temperature reaction with steam and oxygen are quite well known, e.g., the Lurgi process, the Koppers-Totzek proces, etc., and need not be detailed herein. A catalytic steam gasification process for conversion of coal to methane-rich gas by reaction with steam in the presence of certain alkali carbonate catalysts at about 600°–750° C is described in U.S. Pat. No. 3,686,240 to Aldridge et al. In general, all of these coal gasification processes are endothermic in the gasification stage and produce a suitable gas feed mixture for methanation according to the instant invention even though the $H_2O$ content may range as high as 50% by weight of the feed mixture, a value at or near methanation equilibrium for conventional supported methanation catalysts. This feed mixture is suitable for high temperature methanation with the instant catalysts because, as indicated previously, the molten salt carriers of the instant invention have the ability to absorb up to over 90% of the water present in the methanation feed gas, thereby shifting the reaction equilibrium towards methane. It is especially preferred that the instant methanation process be utilized to upgrade the methane content of the gaseous effluent derived from a coal-steam gasification process such as that described in the aforementioned U.S. Pat. No. 3,686,240 since the endothermic gasification takes place at a temperature approximating the exothermic methanation temperature. Thus, it is possible to utilize the heat generated by methanation via for example, heat exchange between the molten salt carrier and the gasification reaction zone, to at least partially satisfy the heat requirements of the gasification reaction.

Procedurally, the methanation process of the instant invention can be suitably effected by any conventional technique for intimately contacting a gaseous reactant feed with a molten or fluid catalyst. Such techniques include batch or continuous procedures wherein the gas is introduced into the vapor phase of a reaction chamber or autoclave containing the molten salt-based catalyst and the catalyst is agitated into contact with the gas mixture. In the case of a batch reaction according to this procedure the product gas is merely withdrawn at the end of the reaction (measured by time and/or pressure drop) whereas in the case of a continuous reaction the size of the reaction chamber and catalyst to gas mass ratios in the reaction chamber are selected to allow sufficient gas-molten medium contact prior to continuous withdrawal of product gas at some point in the vapor phase remote from the reactant feed port. Alternatively, the gas phase can be bubbled through a mass of molten catalyst in a reaction chamber or autoclave or passed into countercurrent contact with the catalyst phase in a vertically-oriented contacting column. In any case, the methanation reaction zone is maintained at temperatures above about 500° C while the gaseous reactant feed mixture is in contact with the catalyst. Preferably, the methanation reaction according to this invention is effected at temperatures between about 500° and 900° C and most preferably between about 600° and 800° C. The pressures employed in the methanation reaction according to the invention generally range between 100 psig and 1500 psig and preferably between 400 and 1200 psig.

The reaction or gas-molten salt contact time is not considered critical to the operation of the methanation process of the instant invention, provided sufficient time is alloted to facilitate adsorption of water into the molten salt carrier and mass transfer and adsorption of the gaseous reactants on to the active catalytic species dispersed in the molten carrier. Accordingly, the reaction time should be at least about 10 seconds with reaction times of about 10 minutes being a reasonable maximum for practical operation. Preferably, the reaction time ranges from about 0.5 to about 5 minutes. In this regard the ratio of volume of reactant feed gas to molten salt-based catalyst in continuous processes employing the methanation catalysts of the invention may suitably range from about 100 to about 5000 per hour (gas measured at STP).

EXAMPLE I

A number of molten salt-based catalyst systems according to the invention were evaluated for catalytic methanation activity in a continuous flow reaction system. In these experiments, the salt catalyst carrier (ca. 100 ml) was added to a methanation reaction chamber comprising a 300 ml Magna-Drive autoclave made of 316 stainless steel, Inconel or Hastelloy B, the salt carrier was heated to its melting point (usually 400° C or above) and the active catalyst was added to the molten salt carrier under agitation as a metal and/or metal oxide powder or in the form of a decomposable, metal compound or complex catalyst precursor. After heating to methanation reaction conditions (500° C or above), the methanation reactant gas containing hydrogen and carbon monoxide in a 2:1 mole ratio of $H_2$:CO and trace amounts of carbon dioxide and water was continuously introduced into the reaction chamber at a constant elevated pressure (about 400 psig) with the reactant flow rates being controlled at about 30 l/hr or reactant gas by adjusting the pressure drop across long lengths of stainless steel capillary tubing. During each reaction period the molten salt based catalyst was agitated at about 1800 rpm and the reaction temperature was controlled between about 500° and about 650° C with a single-point Thermoelectric[R] controller. The reaction chamber pressure was controlled at a constant level (usually about 400 psig) by a Grove back-pressure regulator placed on the product gas exit line from the reaction chamber. Exit gases from the reaction chamber were continuously withdrawn at a constant rate during the reaction period and subjected to analysis by gas chromatography and mass spectrometry.

Various catalytically active metals and metal salt-based carriers were tested at a variety of different catalyst concentrations in continuous flow test runs which ranged from 3 to 24 h in duration. The results of these tests including further descriptions of the catalyst systems and the relative conversions to methane (usually ignoring carbon dioxide in the exit gas, which introduces a slight error of about 10% in the 600° C experiments due to contribution from the CO-shift reaction) are given in Table I below.

ucts. In these batch experiments the reactant charge (2:1 mole ratio of $H_2$:CO) was charged into the reactor until a given pressure, i.e., 400 psig, was obtained and the system was sealed off. The rate of the methanation reaction in this sealed system was followed by observing the rate of pressure drop in the reactor which results from the conversion of 4 moles of starting material to 2 moles of products. This reaction analysis method gives a good relative measure of the catalyst activity for methanation because the CO-shift reaction which also occurs to a certain extent gives no change in pressure since the mole of product equal the moles of reactants. The results of this series of batch or static methanation reac- Table I

| Run | Metal, Metal Oxide and/or Metal Carbide Catalysts of Elements | Molten Salt Carrier | Catalyst Precursor |
|---|---|---|---|
| 1 | None (carborundum chips) | None | — |
| 2 | Manganese | $ZnI_2$ | $MnI_2$ |
| 3 | Iron | $ZnBr_2$ | $Fe(CO)_5$ |
| 4 | Iron | $ZnBr_2$ | $Fe(CO)_5$ |
| 5 | Iron | $ZnBr_2$ | Ferrocene |
| 6 | Iron | $ZnBr_2$ | Ferrocene |
| 7 | Iron | $ZnBr_2$ | Ferrocene |
| 8 | Iron | $ZnCl_2$[a] | $FeCO_5$ + Ferrocene |
| 9 | Molybdenum | 5/1 CuBr/KBr | $Mo(CO)_6$ |
| 10 | Iron | 2/1 $FeCl_2$/KCl | $Fe(CO)_5$ |
| 11 | Iron | $SnCl_2$ | $Fe(CO)_5$ |
| 12 | Molybdenum | $Li_2CO_3/Na_2CO_3/K_2CO_3$[b] | $Mo(CO)_6$ |
| 13 | Cobalt | $Li_2CO_3/Na_2CO_3/K_2CO_3$[b] | $CoCO_3$ |
| 14 | Iron | $Li_2CO_3/Na_2CO_3/K_2CO_3/CaCO_3$[c] | Ferrocene |
| 15 | Zinc | $ZnBr_2$ | Zinc Powder |
| 16 | Manganese | $LiCO_3/Na_2CO_3/K_2CO_3$[b] | $MnCO_3$ |
| 17 | Nickel | $ZnI_2$ | Nickel Powder |
| 18 | Nickel | $ZnBr_2$ | Nickel Powder |

| Run | Catalyst concentration %w elemental metal based on weight of catalyst plus carrier | Total weight catalyst plus carrier (grams) | Reaction Temperature | % conversion of carbon monoxide to methane |
|---|---|---|---|---|
| 1 | None | None | 600° C | 5 |
| 2 | 7 | 300 | 600° C | 39 |
| 3 | 3 | 300 | 500° C | 25 |
| 4 | 3 | 300 | 600° C | 45 |
| 5 | 2 | 300 | 500° C | 24 |
| 6 | 2 | 300 | 550° C | 33 |
| 7 | 2 | 300 | 600° C | 41 |
| 8 | 3 | 270 | 500° C | 26 |
| 9 | 2 | 370 | 500° C | 19 |
| 10 | 2 | 290 | 500° C | 28 |
| 11 | 2 | 330 | 500° C | 24 |
| 12 | 6 | 300 | 600° C | 30 |
| 13 | 1 | 250 | 600° C | 50 |
| 14 | 2 | 300 | 600° C | 36 |
| 15 | 2 | 300 | 600° C | 44 |
| 16 | 5 | 260 | 600° C | 38 |
| 17 | 5 | 300 | 600° C | 20 |
| 18 | 4 | 300 | 600° C | 12 |

[a]ca. 4% by weight ammonia added to molten salt catalyst system.
[b]eutectic mixture of alkali metal carbonates, i.e., $LiCO_3/Na_2CO_3K_2CO_3$ at a weight ratio of 87/75/90.
[c]eutectic mixture of alkali metal carbonates plus ca. 10% by weight $CaCO_3$.

EXAMPLE II

A series of batch or static methanation reactions were carried out with various molten salt-based catalyst systems according to the invention. These experiments were carried out utilizing a reaction system and procedure which was similar to that described in Example I in all regards except the manner of reactant introduction and the analysis performed on the reaction prodtions is recorded in Table II below wherein relative ratings are given for the activities — e.g., high, medium or low — of the catalysts evaluated. As a rule of thumb, a "high" activity rating was given to those catalyst systems which gave more than fifty percent conversion of CO to $CH_4$ in less than ten minutes whereas the lowest rating, i.e., "very low" for activity means less than a 10 percent conversion over a reaction time of 1 hour or more.

Table II

| Run | Metal, Metal Oxide and/or Metal Carbide Catalysts of Elements | Molten Salt Carrier | Catalyst Precursor |
|---|---|---|---|
| 19 | Iron | $ZnBr_2$ | $Fe_2(CO)_9$ |
| 20 | Iron | $LiCO_3/Na_2CO_3/K_2CO_3$[a] | $Fe_2(CO)_9$ |

Table II-continued

| Run | | | |
|-----|--------|-------------|------------------|
| 21 | Iron | FeCl$_2$/NaCl | Fe(CO)$_5$ |
| 22 | Nickel | ZnBr$_2$ | Ni(C$_5$H$_5$)$_2$ |
| 23 | Zinc | ZnBr$_2$ | ZnBr$_2$/Na$_2$CO$_3$ |
| 24 | Iron | ZnBr$_2$ | Iron Powder |
| 25 | Manganese | MnCl$_2$/NaCl | MnCl$_2$ |
| 26 | Silver | LiCO$_3$/Na$_2$CO$_3$/K$_2$CO$_3$[a] | Ag$_2$O |
| 27 | Iron | LiCl/liF | Fe(CO)$_5$ |
| 28 | Titanium | ZnBr$_2$ | TiO$_2$ |
| 29 | Thorium | ZnBr$_2$ | ThO$_2$ |
| 30 | Thorium | FeCl$_2$/NaCl | ThO$_2$ |
| 31 | Iron | CaCl$_2$/LiCl | Iron Powder |
| 32 | Copper | FeCl$_2$/NaCl | Cu$_2$S |
| 33 | Iron | ZnBr$_2$ | Fe(OH)$_2$ |

| Run | Catalyst concentration %w elemental metal based on weight of catalyst plus carrier | Total weight catalyst plus carrier (grams) | Reaction Temperature °C | Relative Activity for methanation |
|-----|------|-----|---------|-----------------|
| 19 | 1.8 | 306 | 500,600 | high |
| 20 | 1.1 | 258 | 500,600 | moderately high |
| 21 | 2.8 | 201 | 500 | high |
| 22 | 1.0 | 303 | 500 | moderately high |
| 23 | 2.1 | 306 | 600 | medium |
| 24 | 1.8 | 306 | 500,600 | high |
| 25 | 26 | 190 | 600 | low |
| 26 | 7.9 | 272 | 600 | low |
| 27 | 1.8 | 306 | 600 | high |
| 28 | 1.6 | 305 | 600 | moderately low |
| 29 | 3.7 | 311 | 600 | moderately low |
| 30 | 5.6 | 205 | 600 | moderately low |
| 31 | 4.1 | 136 | 600 | very low |
| 32 | 1.6 | 202 | 600 | low |
| 33 | 0.9 | 303 | 500,600 | high |

[a]eutectic mixtures of alkali metal carbonates, i.e., LiCO$_3$/Na$_2$CO$_3$/K$_2$CO$_3$ at a weight ratio of 87/75/90.

EXAMPLE III

A series of absorption experiments were performed to demonstrate the ability of various molten salt carriers according to the invention to absorb water at the high temperatures utilized in the methanation process according to the invention, i.e., 500° C and above and thereby shift the methanation reaction equilibrium towards methane formation. In these experiments the molten salts and water (at steam) were held in a small 310 stainless steel autoclave equipped with an electric heater, thermowell and pressure gauge. Sealing was achieved through use of a copper gasket which was compressed upon heating and upon cooling as the various parts of the vessel expand and contract. Connecting lines to the pressure gauge were heated to prevent condensation anywhere in the system. After adding the salt and water to the autoclave, pressure was recorded as the apparatus was heated with occasional shaking to the maximum temperature desired, near 600° C. The apparatus was then allowed to cool and heated up again. This procedure helped to assure attainment of equilibrium and allowed corrections to be made for gas produced through hydrolysis of salts or corrosion of the vessel. The extent of water absorption by the molten salt at equilibrium was obtained by comparing the vapor pressure of the system with that which would be predicted (for the quantity of water added) from Raoult's law (vapor pressure over ideal solution). The results are given in Table III.

Table III

| Molten Salt | Total Water In System %m | % water absorbed by Salt Phase at temperature (° C) | | | |
|---|---|---|---|---|---|
| | | 425 | 475 | 525 | 575 |
| ZnBr$_2$ | 10 | 92 | 90 | 87 | 83 |
| ZnBr$_2$ | 20 | 86 | 86 | 82 | 81 |
| ZnBr$_2$ | 30 | 87 | 85 | 81 | 77 |
| LiCO$_3$/Na$_2$CO$_3$/K$_2$CO$_3$ (Ternary eutectic) | 4 | — | — | 37 | — |

Table III-continued

| Molten Salt | Total Water In System %m | % water absorbed by Salt Phase at temperature (° C) | | | |
|---|---|---|---|---|---|
| | | 425 | 475 | 525 | 575 |

What is claimed is:

1. A process for the production of methane from a gaseous reactant mixture containing hydrogen and a compound selected from the group consisting of carbon monoxide, carbon dioxide, and mixtures thereof, which comprises contacting said gas mixture in a reaction zone maintained at temperatures above about 500° C with a molten metal salt-based catalyst system comprising a molten metal salt carrier melting below 1000° C; said molten salt having dispersed therein one or more catalytically active metals selected from the class consisting of iron, molybdenum, manganese, nickel, cobalt, zinc, titanium, silver, copper and thorium in the form of finely divided elemental metals, metal oxides, metal carbides and mixtures thereof, wherein said molten metal salt carrier is an iron halide.

2. The process of claim 1, wherein the gaseous reactant mixture contains hydrogen and carbon monoxide at an H$_2$:CO mole ratio of at least 2:1.

3. The process of claim 2, wherein the reaction zone is maintained between about 500° and about 900° C.

4. The process of claim 3, wherein the concentration of catalytically active metal dispersed in the molten metal salt carrier ranges from about 0.1 to about 20% by weight of the total catalyst composition.

5. The process of claim 4, wherein said iron halide has a minor amount of alkali metal halide selected from the class consisting of sodium chloride and potassium chloride added thereto as a melting point depressant.

6. The process of claim 4, wherein the catalytically active metal is selected from the class consisting of iron, zinc, manganese and molybdenum.

7. The process of claim 6, wherein the catalytically active metal is zinc or iron.

8. The process of claim 7, wherein the catalytically active metal is zinc.

9. The process of claim 7, wherein the catalytically active metal is iron.

10. The process of claim 1, wherein the gaseous reactant mixture is derived from the partial oxidation or gasification of a carbonaceous fuel.

11. The process of claim 10, wherein the gaseous reactant mixture contains up to about 50% by weight $H_2O$.

* * * * *